(12) United States Patent
Müller

(10) Patent No.: US 6,885,459 B2
(45) Date of Patent: *Apr. 26, 2005

(54) APPARATUS AND METHOD FOR MEASURING TWO OPPOSITE SURFACES OF A BODY

(75) Inventor: Dieter Müller, Binzen (DE)

(73) Assignee: Nanopro Luftlager-Produktions-und Messtechnik GmbH, Freiburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/279,692

(22) Filed: Oct. 24, 2002

(65) Prior Publication Data

US 2003/0058453 A1 Mar. 27, 2003

Related U.S. Application Data

(63) Continuation of application No. 09/905,807, filed on Jul. 13, 2001, now abandoned, which is a continuation of application No. 09/521,036, filed on Mar. 8, 2000, now Pat. No. 6,271,925, which is a continuation of application No. 08/930,378, filed on Sep. 24, 1997, now Pat. No. 6,100,977.

(30) Foreign Application Priority Data

Jan. 24, 1996 (DE) .......................................... 196 02 445

(51) Int. Cl.[7] ................................................ G01B 9/02
(52) U.S. Cl. ...................................... 356/503; 356/512
(58) Field of Search .............................. 356/450, 496, 356/503, 511, 512, 513, 514, 521

(56) References Cited

U.S. PATENT DOCUMENTS 5,355,221 A * 10/1994 Cohen et al. ................ 356/497
5,684,594 A * 11/1997 Platten et al. ............... 356/521
5,889,591 A * 3/1999 Bruning ....................... 356/512
5,995,226 A    11/1999 Abe et al.
6,504,615 B1    1/2003 Abe et al.

FOREIGN PATENT DOCUMENTS

| EP | 0 874 215 A2 | 10/1998 |
| JP | 57-182604 | 11/1982 |
| JP | 361023902 A | 2/1986 |
| JP | 62-106310 | 5/1987 |
| JP | 404221704 A | 8/1992 |
| JP | 408313206 A | 11/1996 |
| JP | 11-2512 | 1/1999 |
| JP | 2963890 | 8/1999 |
| JP | 2000-105101 | 4/2000 |
| JP | 02000105114 A | 4/2000 |
| JP | 09-154023 | 8/2002 |

* cited by examiner

Primary Examiner—Andrew H. Lee
(74) Attorney, Agent, or Firm—George W. Neuner; Edwards & Angell, LLP

(57) ABSTRACT

An apparatus and a method are provided which allow two opposite plane surfaces of a body to be interferometrically measured simultaneously using light from a single light source. From a parallel light beam (P) produced by a light source (1) partial light beams (A, B) having positive and negative diffraction angles are produced using a beam splitter (8) in the form of a diffraction grating. The partial light beams strike the respective surfaces (90, 91) of the body (9) to be measured and are reflected thereat. The reflected partial light beams (A, B) are interfered with the throughgoing partial light beam (P) having an order of diffraction of zero and the thus produced interference patterns are digitized and subtracted from each other, whereby the parallelism of both surfaces (90, 91) of the body can be determined.

9 Claims, 3 Drawing Sheets

APPARATUS AND METHOD FOR MEASURING TWO OPPOSITE SURFACES OF A BODY

Continuation of prior application Ser. No.: 09/905,807, filed Jul. 13, 2001 now abandoned Which is a: Continuation of prior application Ser. No.: 09/521,036, filed Mar. 8, 2000 now U.S. Pat. No. 6,271,928 Which is a: Continuation of prior application Ser. No.: 08/930,378, filed Sep. 24, 1997, now U.S. Pat. No. 6,100,977.

The invention relates to an apparatus and a method for measuring two opposite surfaces of a body according to the preamble of claim 1 or 20, resp.

The technical progress of the semiconductor industry in the last years resulted in a sharp increase of the diameters of the semiconductor wafers as base material for chip production for economic and process technical reasons. Wafers having a diameter of 200 millimeters are already state of the art and wafers having a diameter of 300 millimeters will be processed in near future.

At present manufacturers and processors of such wafer sizes do not yet have measuring devices at their disposal which enable them to check particular quality features such as the geometry (flatness, curvature, thickness variation) of the wafer with a desired resolution and precision.

Two measuring methods for measuring the geometry of semiconductor wafers are known. The one measuring method is an optical geometry measurement using interferometry. One entire surface of the wafer is interferometrically measured, while the wafer rests on a plane plate or is sucked thereto. After measuring one surface the wafer is turned around and the other surface is measured. Since, in this method, one side only can be measured at a time, the relation between the front and rear side of the wafer indicating the parallelism and the thickness variation is not directly given. It is assumed that the sucked surface is drawn in an absolutely plane state, but this is practically not the case, because it is prevented by particles between the wafer and the support and it is generally uncertain whether the wafer—especially in case of unevenness—fits in a uniform manner. Furthermore, a horizontally placed wafer having a diameter of 200 millimeters or 300 millimeters is bent by gravity and therefore no forcefree state of the wafer prevails. This renders the measurement of the absolute evenness impossible. Moreover, the risk of damage due to the surface contact with the support and possibly also with the optical measuring system is so high that mostly sample measurements only are admitted. Owing to the sum of the many measuring uncertainties the measuring accuracy is insufficient. Measurement values produced with other methods are not directly comparable also.

A further method is the capacitive geometry measurement including scanning the surface using distance sensors. Dot scanning distance sensors scan the front side and the rear side of a wafer. The wafer is supported at its center and rotated. Since the measurement is punctual, it is necessary to scan in order to obtain two-dimensional data. The known disadvantages of a scanning method, e.g. instable measuring conditions during the entire scanning process, considerably reduce the measuring accuracy. Since the wafer is centrally supported during the measurement, the gravity exerts a strong influence on the form of the wafer by causing a flexion. This influence can be computationally taken into consideration only to an insufficient approximation. Furthermore, the number of measurement points which can be obtained within an acceptable time is too low. The size of the measurement points resulting from the method and from the sensor diameter can not be reduced to an extent necessary to meet the new quality rules. Moreover, the risk of damaging the wafer is high because of the surface contact and of the very small distance of the sensors to the wafer surface for technical reasons. Generally, also in this case the measuring accuracy is too low, owing to the sum of measuring uncertainties. Again, measuring values produced with other methods can not be directly compared.

It is the object of the invention to provide an apparatus and a method for measuring two opposite, substantially plane and parallel surfaces of a body, in particular of a semiconductor wafer, whereby the measuring accuracy can be increased, the damaging risk can be reduced and the measuring time can be decreased.

The object is achieved by an apparatus according to claim 1 and a method according to claim 20, resp.

Further developments of the invention are defined in the subclaims.

The apparatus and the method, resp., has the following advantages:

The front side and the rear side are measured under absolutely equal conditions in a contactless, isochronal and static manner—no wafer movement occurs—and a single sensor is used. No tuning calibration is required. During the measurement the wafer is free of effects from outer forces, because it stands in an upright position. The critical surfaces of the wafer are never touched, and there is therefore a low risk of damage. All required geometry data are derived from a single measurement. Owing to the single measurement the measuring time is considerably reduced, whereby the throughput and the productivity is increased. The measuring accuracy and the resolution in lateral as well as vertical direction are as high as, or even higher than, required by international standards. Moreover, the method detects the wafer in an unaffected state and could therefore form a standard.

Further features and advantages of the invention will be apparent from a description of an embodiment with reference to the Figures.

Figure 1:
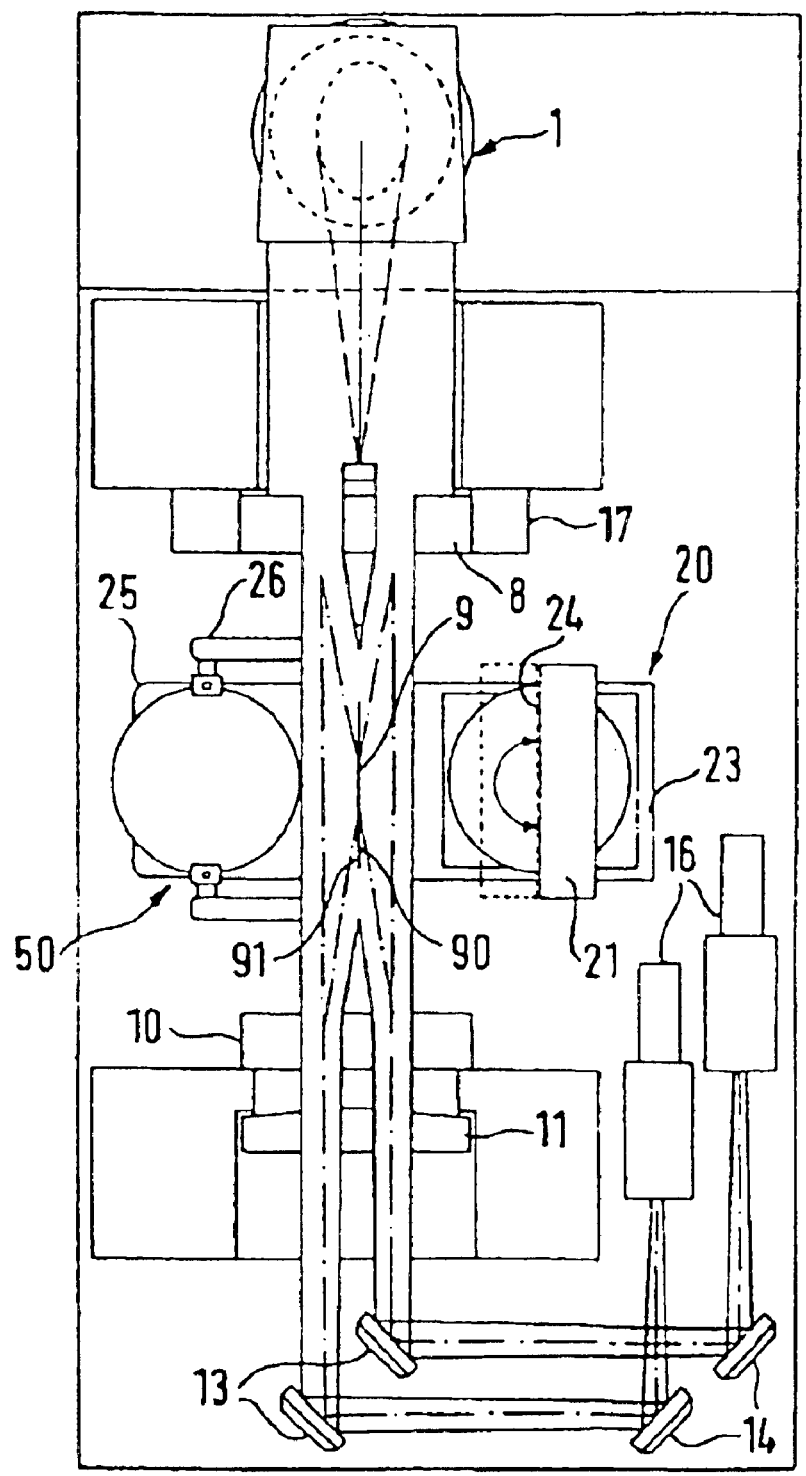
FIG. 1 is a schematic representation of the apparatus.
Figure 2:
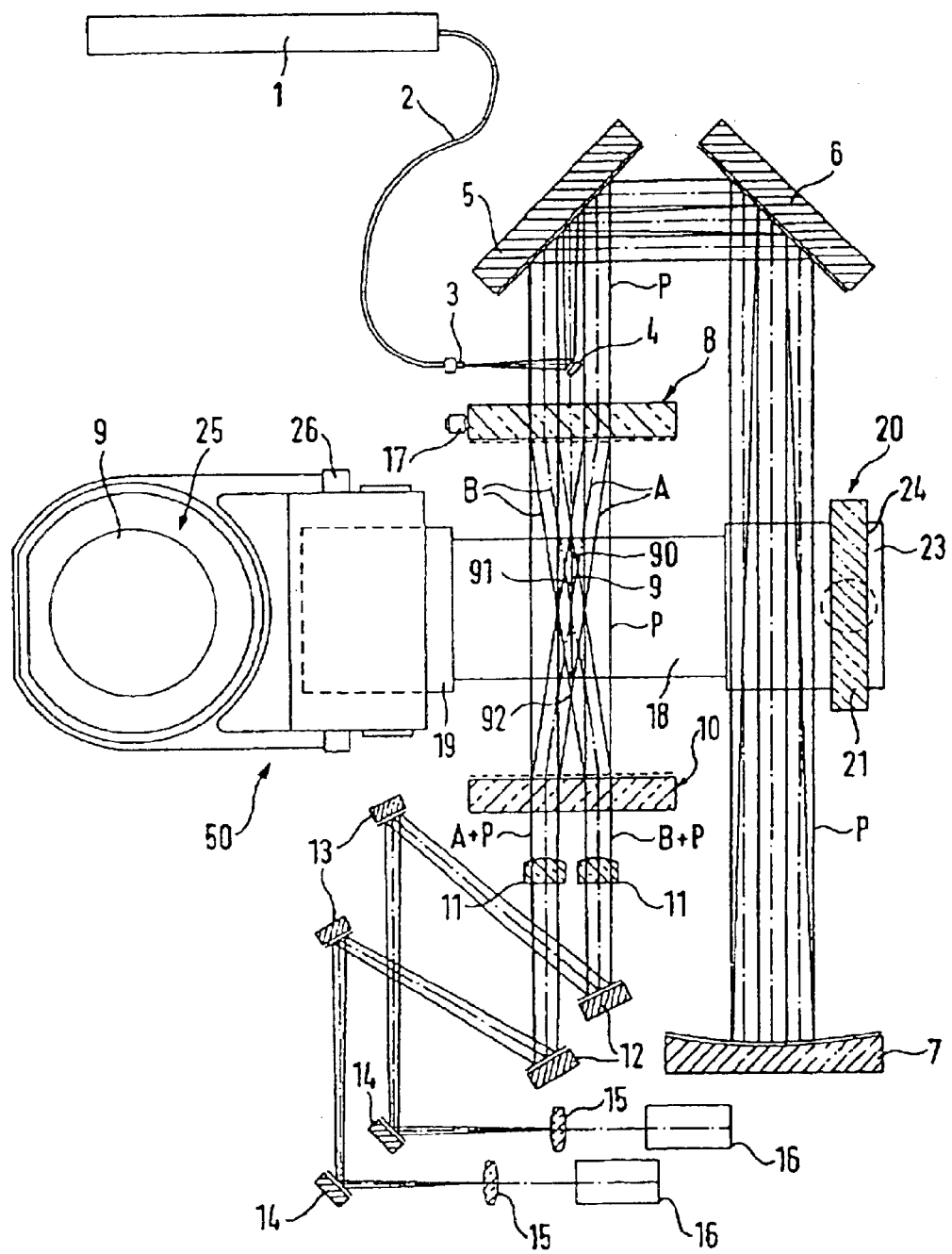
FIG. 2 is a top view of the apparatus showing the path of the rays.

As shown in the FIGS. 1 and 2 the apparatus comprises a light source in the form of a laser 1. The light emitted from the laser 1 is conducted through a beam waveguide 2 to a defined place of the apparatus. The light produced by the laser 1 emerges at an end 3 of the beam waveguides 2 so that the end 3 acts as a punctual light source. The emerging light strikes a deviation mirror 4 wherefrom it is redirected onto a collimation mirror 7 in the form of a parabolic mirror by two further deviation mirrors 5 and 6 which are oriented at an angle of 90° relative to each other. The parallel light beam P reflected from the parabolic mirror 7 reaches a beam splitter 8 through the two deviation mirrors 5 and 6. This beam splitter is formed as a first diffraction grating and is preferably a phase grid. The beam splitter 8 is arranged in the apparatus in a vertical direction and the parallel light beam P strikes the diffraction grating in a perpendicular direction. A beam collector 10 in the form of a second diffraction grating is disposed in a distance from the first diffraction grating and parallel thereto. Behind the beam collector 10 two decollimation lenses 11 are arranged at equal level and the light beams leaving these decollimation lenses are each deflected and focused onto two CCD cameras 16 through deviation mirrors 12, 13, 14 and an optical imaging system 15.

The beam splitter 8 is supported transversely to the optical axis and further comprises a piezoelectric actuating element 17 for shifting the phase of the parallel light beam P by displacing the diffraction grating.

A holding device 50, for example in the form of a support post, is provided centrally between the first diffraction grating and the second diffraction grating. A wafer 9 to be measured is held on the holding device 50 in such a manner that both plane surfaces 90, 91 thereof are arranged in vertical direction parallel to the light beam P. The wafer 9 is supported by the support post substantially at its vertical edge 92 only so that both surfaces 90, 91 are not substantially contacted by the support post and are freely accessible to the interferometric measurement.

Moreover, a receiving device (50, 25) is provided for the wafer 9 to be measured. The wafer can be inserted into the receiving device in a horizontal position. By means of a tilting device 26 the wafer 9 may be tilted from its horizontal position into the vertical measuring position, and the wafer 9 may be transferred, by means of a positionable traveller, into the light path between the first diffraction grating and the second diffraction grating so that the surfaces 90, 91 to be measured are aligned substantially parallel to the undiffracted light beam P and in a substantially vertical direction.

Furthermore, a reference apparatus 20 is provided which comprises a reference body 21 having at least one plane surface 24. The reference body 21 can be introduced into the light path between the first diffraction grating 8 and the second diffraction grating 10 in place of the semiconductor wafer 9 to be measured by means of a traveller 23 with a linear guide 18. The reference body 21 is held so that its plane surface 24 is arranged in vertical direction parallel to the undiffracted light beam P. The reference body 21 can be turned by 180° in its mounting around an axis parallel to its surface 24.

Figure 3:
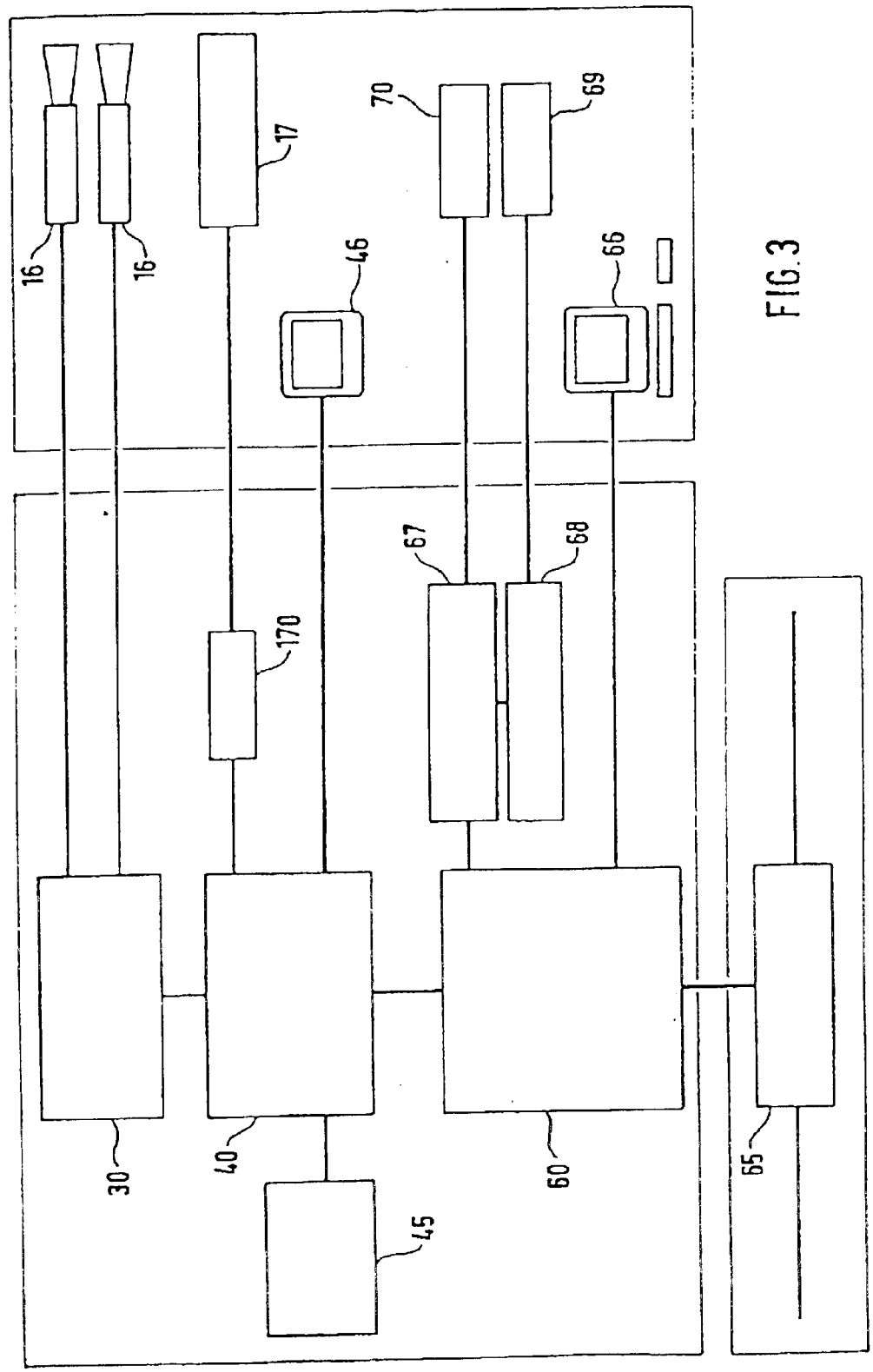
FIG. 3 is a block diagram of the evaluation and operation unit.

As shown in particular in FIG. 3 the apparatus further comprises an electronic device 30 connected to the outputs of the CCD cameras for processing the interference patterns produced by the CCD cameras. The image processing device 30 is further connected to an evaluating processor 40. The evaluating processor 40 is further connected to the phase shifter 17 through a piezo drive member 170. A printer 45 and a video monitor 46 for outputting data are connected to the evaluating processor 40. The evaluating processor 40 is further connected with a master and control unit 60 which is in turn connected with a host computer 65, an operator terminal 66 and the output of an SPC (stored program control) and positioning control. Inputs of the SPC and positioning control are each connected to power electronics 68 for the motors 69 of the travellers for the semiconductor wafer or reference body, resp., to be measured or for moving other mechanical parts of the apparatus. A further input of the SPC and positioning control 67 is connected to the sensor members 70 for the travellers and tilting devices, resp.

In operation the wafer 9 to be measured is first inserted into the wafer receiving device 25. The surfaces 90, 91 to be measured of the wafer 9 are horizontally arranged. By means of the tilting device and of the traveller 19 the wafer to be measured is brought into the holding device 50 where it is arranged so that the surfaces 90, 91 to be measured are vertical. A diffraction of the parallel light beam P striking the first diffraction grating 8 of the beam splitter produces partial light beams A, B, whereby the partial light beam A having a positive diffraction angle strikes the one surface 90 of the wafer and is reflected thereat, whereas the partial light beam B with a negative diffraction angle strikes the other surface 91 of the wafer and is reflected thereat. The 0-th diffraction order of the parallel light beam P passes through the first diffraction grating 8 and is not reflected at the surfaces 90, 91 of the wafer 9. This partial light beam P serves as reference beam for interference with the reflected wave fronts of the beams A and B. In the second diffraction grating 10, the beam collector, the reflected partial light beams A and B, resp., are each combined again with the reference beam P of the 0-th diffraction order and focused, in the form of two partial light beams A+P and B+P, resp., onto the focal planes of the CCD cameras 16 through decollimation lenses 11 and deviation mirrors 12, 13 and 14 as well as positive lenses 15.

During the exposure of the surfaces the phase of the parallel light beam P is repeatedly shifted by 90° and 120°, resp., by displacing the diffraction grating. This produces phase shifted interference patterns. The output data of the CCD cameras 16 are fed to the image processing device 30 which produces digitized phase patterns 160 for each measured surface 90, 91 on the basis of the individual interference patterns of the CCD cameras 16. The digitized phase patterns 160 are further processed in the evaluation processor 40 and imaged on the video monitor 46. The defined shift of the interference phase produced by the phase shifter 17 is evaluated to determine whether there is a protuberance or a depression in the measured surfaces 90, 91. For determining the parallelism of the measured surfaces 90, 91 the two digitized phase patterns are subtracted from each other. Moreover, a mask for the phase patterns is generated in the evaluation processor and the phase patterns are calibrated, parametrized and stored in the evaluation processor. The generated graphics and tables can be outputted via the printer 45.

A calibration using the reference body 21 can be performed before each measurement of a wafer 9. The reference body 21 is introduced into the beam path between the first diffraction grating 8 and the second diffraction grating 10 and the known plane surface 24 is measured. Subsequently the reference body 21 is turned by 180° and the same surface 24 is measured as a second surface.

Modifications of the apparatus and of the method are possible. A body having two precisely plane parallel surfaces may be used for the reference body 21, whereby both surfaces are measured simultaneously. However, the embodiment having a single plane surface of the reference body is more suitable.

What is claimed is:

1. A method of measuring two opposite surfaces of a semiconductor wafer, comprising:
    maintaining said wafer in an upright, static position;
    exposing a front side and a rear side of said wafer to light, wherein said light reflects from said front side and said rear side of said wafer;
    forming digitized phase patterns from said reflected light; and
    comparing said digitized phase patterns to determine the parallelism of said front side and said rear side of said wafer.

2. The method according to claim 1, wherein the light is a beam and the wafer is arranged in the beam path so that the surfaces to be measured are aligned substantially in a vertical direction.

3. The method according to claim 1, wherein the light is split into three partial light beams by means of a beam splitter, whereby two of the partial light beams are deflected each on one of the two opposite surfaces to be measured and reflected therefrom and the third partial light beam is used as a reference beam for the interference measurement.

4. The method according to claim 3, wherein the two of the partial light beams striking the surfaces to be measured are produced by diffraction at a grating, whereby one the partial light beam has a positive diffraction angle and is used for measuring the one surface and the second partial light beam has a negative diffraction angle and is used for measuring the opposite surface, and whereby the third partial light beam has a diffraction angle of zero is used as a reference beam.

5. The method according to claim 1, further comprising producing several phase-shifted interference patterns of each surface to be measured.

6. The method according to claim 3, further comprising shifting the phase of the partial light beams by a defined phase angle using a phase shifter for producing moving phase patterns for determining protuberances or depressions in the surfaces to be measured.

7. The method according to claim 5, further comprising subtracting the phase patterns of both surfaces are subtracted from each other for determining the parallelism of the surfaces.

8. The method according to claim 1, further comprising making a calibration measurement, whereby a reference body having at least one plane surface is brought into the measurement position and the plane surface is measured.

9. The method according to claim 8, further comprising turning the reference body by 180° around an axis parallel to the plane surface and measuring the plane surface again.

* * * * *